(12) United States Patent
Siva Kimar et al.

(10) Patent No.: US 10,497,464 B2
(45) Date of Patent: Dec. 3, 2019

(54) METHOD AND DEVICE FOR IN SILICO PREDICTION OF CHEMICAL PATHWAY

(71) Applicant: Samsung Electronics Co., Ltd, Suwon-si, Gyeonggi-do (KR)

(72) Inventors: Tadi Venkata Siva Kimar, Bangalore (IN); Anirban Bhaduri, Bangalore (IN); Taeyong Kim, Daejeon (KR); Varun Giri, Bangalore (IN)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 428 days.

(21) Appl. No.: 15/334,126

(22) Filed: Oct. 25, 2016

(65) Prior Publication Data

US 2017/0121852 A1 May 4, 2017

(30) Foreign Application Priority Data

Oct. 28, 2015 (IN) .......................... 5812/CHE/2015
Mar. 3, 2016 (KR) ........................ 10-2016-0025779

(51) Int. Cl.
| | |
|---|---|
| *G01N 33/48* | (2006.01) |
| *G01N 33/50* | (2006.01) |
| *G16B 35/00* | (2019.01) |
| *G16C 20/60* | (2019.01) |
| *G16C 20/30* | (2019.01) |
| *G16C 20/10* | (2019.01) |

(52) U.S. Cl.
CPC ............ *G16B 35/00* (2019.02); *G16C 20/10* (2019.02); *G16C 20/30* (2019.02); *G16C 20/60* (2019.02)

(58) Field of Classification Search
None
See application file for complete search history.

(56) References Cited

U.S. PATENT DOCUMENTS

| | | |
|---|---|---|
| 8,401,797 B2 | 3/2013 | Hlavacek et al. |
| 8,413,065 B2 | 4/2013 | Horodezky |
| 2008/0177478 A1 | 7/2008 | Hlavacek et al. |

FOREIGN PATENT DOCUMENTS

| | | |
|---|---|---|
| JP | 2011175454 A | 9/2011 |
| WO | 2009/118845 A1 | 1/2009 |

OTHER PUBLICATIONS

Campodonico et al., Generation of an atlas for commodity chemical production in *Escherichia coli* and a novel pathway prediction algorithm, GEM-Path, *Metabolic Engineering*, 25:140-158 (2014).
Cho et al., Prediction of novel synthetic pathways for the production of desired chemicals, *BMC Systems Biology*, 4(35): 1-16 (2010).
McClymont et al., Metabolic tinker: an online tool for guiding the design of synthetic metabolic pathways, *Nucleic Acids Research*, 41(11): 1-9 (2013).
Yim et al., Metabolic engineering of *Escherichia coli* for direct production of 1,4-butanediol, *Nature Chemical Biology*, 7: 445-452 (2011).

*Primary Examiner* — Russell S Negin
(74) *Attorney, Agent, or Firm* — Leydig, Voit & Mayer, Ltd.

(57) ABSTRACT

Disclosed are a method and device for multi-directionally predicting a plurality of output molecules through reaction prediction steps, computing similarity between the multi-directionally predicted output molecules, and using the generated data to predict chemical pathways.

10 Claims, 18 Drawing Sheets

FIG. 7

|    | R1 | R2 | R3 | R4 |
|----|----|----|----|----|
| F1 |    |    |    |    |
| F2 |    |    |    |    |
| F3 |    |    |    |    |
| F4 |    |    |    |    |

TRANSFORAMTION RULE MATRIX (T)

·

|    |    |
|----|----|
| C1 |    |
| C2 |    |
| C3 |    |
| C4 |    |

COEFFICIENT VECTOR (C)

=

| Dif |    |
|-----|----|
| F1  |    |
| F2  |    |
| F3  |    |
| F4  |    |

DIFFERENCE VECTOR (D)

FIG. 8

$$\left( \begin{array}{c|cccc} & R1 & R2 & R3 & R4 \\ \hline CH & -1 & 0 & 0 & 0 \\ C(OH) & 1 & -1 & 0 & 0 \\ C(=O) & 0 & 1 & -1 & -1 \\ C(=O)OH & 0 & 0 & 1 & 0 \\ C(=O)SCoA & 0 & 0 & 0 & 1 \end{array} \right)^{-1} \cdot \begin{array}{c|c} & Dif \\ \hline CH & -1 \\ C(OH) & 0 \\ C(=O) & 0 \\ C(=O)OH & 1 \\ C(=O)SCoA & 0 \end{array} = \begin{array}{c|c} C1 & 1 \\ C2 & 1 \\ C3 & 1 \\ C4 & 0 \end{array}$$

COEFFICIENT
VECTOR (C)

METHOD AND DEVICE FOR IN SILICO PREDICTION OF CHEMICAL PATHWAY

CROSS-REFERENCE TO RELATED APPLICATIONS

This application claims the benefits of Indian Patent Application No. 5812/CHE/2015, filed on Oct. 28, 2015, in the Indian Intellectual Property Office, and of Korean Patent Application No. 10-2016-0025779, filed on Mar. 3, 2016, in the Korean Intellectual Property Office, the disclosures of which are incorporated herein in their entireties by reference.

BACKGROUND

1. Field

The present disclosure relates to knowledge-based expert systems and computational synthesis chemistry, and more particularly, to in silico prediction of chemical pathways for transforming an input of a start compound to a target compound.

2. Description of the Related Art

Synthesis or degradation of chemicals through chemical and/or biochemical pathways requires a large number of processes in chemical fields. Recently, studies to resolve complexity or vastness of data required for prediction, identification, and validation of synthetic pathways have been pursued through in silico simulations. In silico simulations associated with novel synthetic chemical pathways may require, for example, two components: one is a robust library of data collected with respect to possible chemical modifications upon various reaction rules; and the other is an efficient system, which is referred to as a chemical transformation processor, dealing with reaction rules to transform input molecules and predict new product molecules.

Processes in the in silico simulation for predicting novel synthetic chemical pathways involve application of the reaction rules to molecules and predicting products or precursors (retro-synthesis). In the case of generating multi-step chemical pathways, the processes can be iterated on all predicted products/precursors found in individual reaction steps. To obtain an appropriate end/start compound in a synthetic pathway, the processes can be iterated for multiple steps. Here, computational intensiveness increases exponentially with each iteration. Thus, the simulation results produce a number of data sets that are almost impossible to manually deal with.

In this regard, there is a demand for an improved method and device for in silico prediction of chemical reactions that can reduce or refine simulation data.

SUMMARY

Provided are a method and device for in silico prediction of a chemical pathway.

Additional aspects will be set forth in part in the description which follows and, in part, will be apparent from the description, or may be learned by practice of the presented embodiments.

According to an aspect of an embodiment, a method for in silico prediction of chemical pathway(s) for transforming start compound(s) to target compound(s) is disclosed. The method starts with multi-directionally predicting output molecule(s), through reaction prediction step(s), produced by each of one or more input(s) using a knowledgebase. The input(s) include start compound(s) and/or target compounds and/or the predicted one or more output molecules. The output molecule(s) produced at a previous reaction prediction step become input for a next reaction prediction step. The output molecule(s) are predicted at each of the reaction prediction steps by applying a set of transformation rule(s), included in the knowledgebase, on the input(s). This is followed by collecting all the multi-directionally predicted output molecule(s) into a set of intermediate molecule(s), after each reaction prediction step. The method further includes computing the similarity between the multi-directionally predicted output molecule(s) within the set of intermediate molecules to create groups of similar multi-directionally predicted output molecule(s) and identifying a representative member for each group of similar multi-directionally predicted output molecule(s). The computation is performed after each of the reaction prediction steps or after a preset number of the reaction prediction steps. The method further includes replacing each group of similar molecules within the set of intermediate molecules with the single representative member, thereby using the representative member of each group of similar molecules and the non-similar multi-directionally predicted output molecule(s) as multi-directionally predicting output molecule(s) inputs for next reaction prediction step. Finally, the method further includes connecting together the start compounds, the multi-directionally predicted output molecule(s), the target compound molecule(s), the multi-directionally predicted output molecule(s), and the sequences of the reaction prediction steps to predict the chemical pathway, thereby reducing redundancy in pathway prediction computation and computed pathway data. The predicted chemical pathway comprise sequential arrangements of the reaction prediction steps governed by the transformation rule(s).

According to an aspect of another embodiment, a device for in silico prediction of one or more chemical pathways for transforming one or more start compounds to one or more target compounds is disclosed. The device includes a memory and processor(s) operatively coupled to the memory. The processors are configured to perform the steps including: (a) multi-directionally predicting output molecule(s), through reaction prediction step(s), produced by each of input(s) using a knowledgebase. The input(s) include start compound(s) and/or target compounds and/or the predicted one or more output molecules. The output molecule(s) produced at a previous reaction prediction step become input for a next reaction prediction step. The output molecule(s) are predicted at each of the reaction prediction steps by applying a set of transformation rule(s), included in the knowledgebase, on the input(s); (b) collecting all the multi-directionally predicted output molecule(s) into a set of intermediate molecule(s), after each reaction prediction step; (c) computing the similarity between the multi-directionally predicted output molecule(s) within the set of intermediate molecule(s) to create groups of similar multi-directionally predicted output molecule(s) and identify a representative member for each group of similar multi-directionally predicted output molecule(s). The computation is performed after each of the reaction prediction steps or after a preset number of the reaction prediction steps; (d) replacing each group of similar molecules within the set of intermediate multi-directionally predicted output molecule(s) with the single representative member, thereby using the representative member of each group of similar molecules and non-similar multi-directionally predicted output molecule(s) as inputs for a next reaction prediction step; and (e) connecting together the start compounds, the target compounds, the multi-directionally predicted output molecule(s), and the sequences of the reaction prediction steps to predict the chemical pathway(s), thereby reducing redundancy in pathway prediction computation and computed pathway data. The predicted chemical pathway comprise sequential arrangement of the reaction prediction steps governed by the transformation rule(s).

According to an aspect of another embodiment, a method for in silico prediction of chemical pathway(s) for transforming start compound(s) to target compound(s) is disclosed. The method steps start with identifying chemical moiety(ies) from the start compound(s) and the target compound(s) received as input. The identification of chemical moieties is performed with reference to a knowledgebase for a pair of the one start compound and the one target compound, formed from the input, at a given time. The method further includes extracting the identified chemical moiety (ies) pertaining to a functional group from each pair of the start and target compound received as input. The method further includes constructing a functional chemical moiety vector representing functional groups for the start and target compound(s) received as input based on the knowledgebase. The method further includes computing a difference between the functional chemical moiety vector of the input target compound and the functional chemical moiety vector of the input start compound. The method further includes computing a transformation vector based on the computed difference between the functional chemical moiety vector of the input target compound and the functional chemical moiety vector of input and a rule transformation matrix. The input is the start compound(s) or the intermediate(s) produced from the input start compound(s) after application of a set of transformation rules listed in the transformation matrix. The method further includes identifying a sequence of transformations from at least one of the start compound(s) and the intermediate(s) to the target compound(s) based on the computed transformation vector. Finally, predicting the chemical pathway(s) based on the sequence of the transformations identified while applying corresponding transformation rule(s), present in the knowledgebase, to the start compound(s) and the intermediate(s) to predict the target compound(s). The chemical pathways comprise sequential arrangements of a plurality of chemical reactions governed by transformation rule(s).

According to an aspect of another embodiment, a device for in silico prediction of chemical pathway(s) for transforming start compound(s) to target compound(s) is disclosed. The device includes a memory and processor(s) operatively coupled to the memory. The processors are configured to perform the steps including: (a) identifying chemical moiety(ies) from the start compound(s) and the target compound(s) received as input. The identification of chemical moieties is performed with reference to a knowledgebase for a pair of one start compound and one target compound, formed from the input, at a given time; (b) extracting the identified chemical moiety(ies) pertaining to a functional group from each pair of a start and target compound received as input; (c) constructing a functional chemical moiety vector representing functional groups for the start and target compound(s) received as input based on the knowledgebase; (d) computing a difference between the functional chemical moiety vector of the input target compound and the functional chemical moiety vector of the input start compound; (e) computing a transformation vector based on the computed difference between the functional chemical moiety vector of the input target compound and the functional chemical moiety vector of input and a rule transformation matrix. The input the start compound(s) or the intermediate(s) produced from the input start compound (s) after application of a set of transformation rules listed in the transformation matrix; (e) identifying a sequence of transformations from at least one of the start compound(s) and the intermediate(s) to the target compound(s) based on the computed transformation vector; and (f) predicting the chemical pathway(s) based on the sequence of the transformations identified while applying corresponding transformation rule(s), present in the knowledgebase, to the start compound(s) and the intermediate(s) to predict the target compound(s). The chemical pathways comprise a sequential arrangement of a plurality of chemical reactions governed by transformation rule(s).

According to an aspect of another embodiment, a method of simplification of chemical pathway(s) for transforming start compound(s) to target compound(s) is disclosed. The method includes the steps of (a) acquiring a plurality of chemical pathways for transforming the start compound(s) to target compound(s), wherein the chemical pathways comprise sequential arrangements of a plurality of chemical reactions governed by one or more transformation rules based on a knowledgebase; (b) identifying at least one of a plurality of the reactions acting on the same reactant and product pair where the plurality of the chemical reactions are predicted using different transformation rules, and a plurality of chemical pathways, formed by the same set of the transformation rules, predicted for transforming the one or more start compounds to one or more target compounds, and a plurality of chemical pathways, having similar intermediates, predicted for transforming the one or more start compounds to one or more target compounds; (c) grouping together at least one of the identified plurality of the reactions acting on the same reactant and product pair, and at least one of the one or more chemical pathways formed by the same set of transformation rules and the one or more chemical pathways having similar intermediates; and (d) simplifying the one or more groups of the one or more chemical pathways for transforming the one or more start compounds to one or more target compounds.

According to an aspect of another embodiment, a device for simplification of chemical pathway(s) for transforming start compound(s) to target compound(s) is disclosed. The device includes a memory and processor(s) operatively coupled to the memory. The processors are configured to perform the steps including: (a) acquiring a plurality of chemical pathways for transforming the start compound(s) to target compound(s), wherein the chemical pathways comprise sequential arrangements of a plurality of chemical reactions governed by one or more transformation rules based on a knowledgebase; (b) identifying at least one of a plurality of the reactions acting on same reactant and product pair where a plurality of the chemical reactions are predicted using different transformation rules, and a plurality of chemical pathways, formed by the same set of the transformation rules, predicted for transforming the one or more start compounds to one or more target compounds, and a plurality of chemical pathways, having similar intermediates, predicted for transforming the one or more start compounds to one or more target compounds; (c) grouping together at least one of the identified plurality of the reactions acting on the same reactant and product pair, and at least one of the one or more chemical pathways formed by the same set of transformation rules and the one or more chemical pathways having similar intermediates; and (d)

simplifying the one or more groups of the one or more chemical pathways for transforming the one or more start compounds to one or more target compounds.

BRIEF DESCRIPTION OF THE DRAWINGS

These and/or other aspects will become apparent and more readily appreciated from the following description of the embodiments, taken in conjunction with the accompanying drawings in which:

FIG. 7 is a diagram illustrating an equation using a transformation rule matrix, according to another embodiment;

FIG. 8 is a diagram illustrating an example of obtaining coefficient vector C according to the equation of FIG. 7;

DETAILED DESCRIPTION

The terms used in the present embodiments are selected from general terms that are now widely available in consideration of functions of the present embodiment. However, these terms may vary depending on an intention of one of ordinary skill in the art, precedent cases, or the appearance of new techniques. In addition, in certain circumstances, these terms are arbitrarily selected, and in this case, the meaning of the terms will be described in detail in the description of the corresponding embodiments. Therefore, the terms used in the present embodiments should not be defined as names of simple terms, but should be defined throughout the meaning of the terms and based on the contents described in the present embodiments.

In the descriptions of the embodiments, it will be understood that when one part is referred to as being connected with another part, it can directly connected with another part or it can be electrically connected with another part and a different component may be present in the middle between the two parts. In addition, it will be understood that when a portion includes an element, another element may be further included, rather than excluding the existence of the other element, unless otherwise described. In addition, the term " . . . member" or " . . . module" used herein refers to a unit for processing at least one function or operation, and can be implemented in hardware, software, or a combination of hardware and software.

It will be further understood that the terms "comprises" or "includes" used herein should not be construed to necessarily include all various components or steps set forth in the specification. These terms will be construed as not including some components or some steps, or as further including additional components or steps.

The descriptions of the embodiments provided below will not be construed as limiting the scope of the present disclosure, and what one of ordinary skill in the art can readily analogize should be construed as belonging to the scope of the embodiments. The embodiments will now be described in detail with reference to the accompanying drawings. The drawings described herein are for illustration purposes only.

An embodiment of the present disclosure provides a method of in silico prediction for a chemical pathway for transforming a start compound to a target compound.

In an embodiment, a method of in silico prediction for a chemical pathway for transforming a start compound to a target compound is described, the method being performed by multi-directionally predicting output molecules that are produced by each input based on a knowledgebase.

Figure 1:
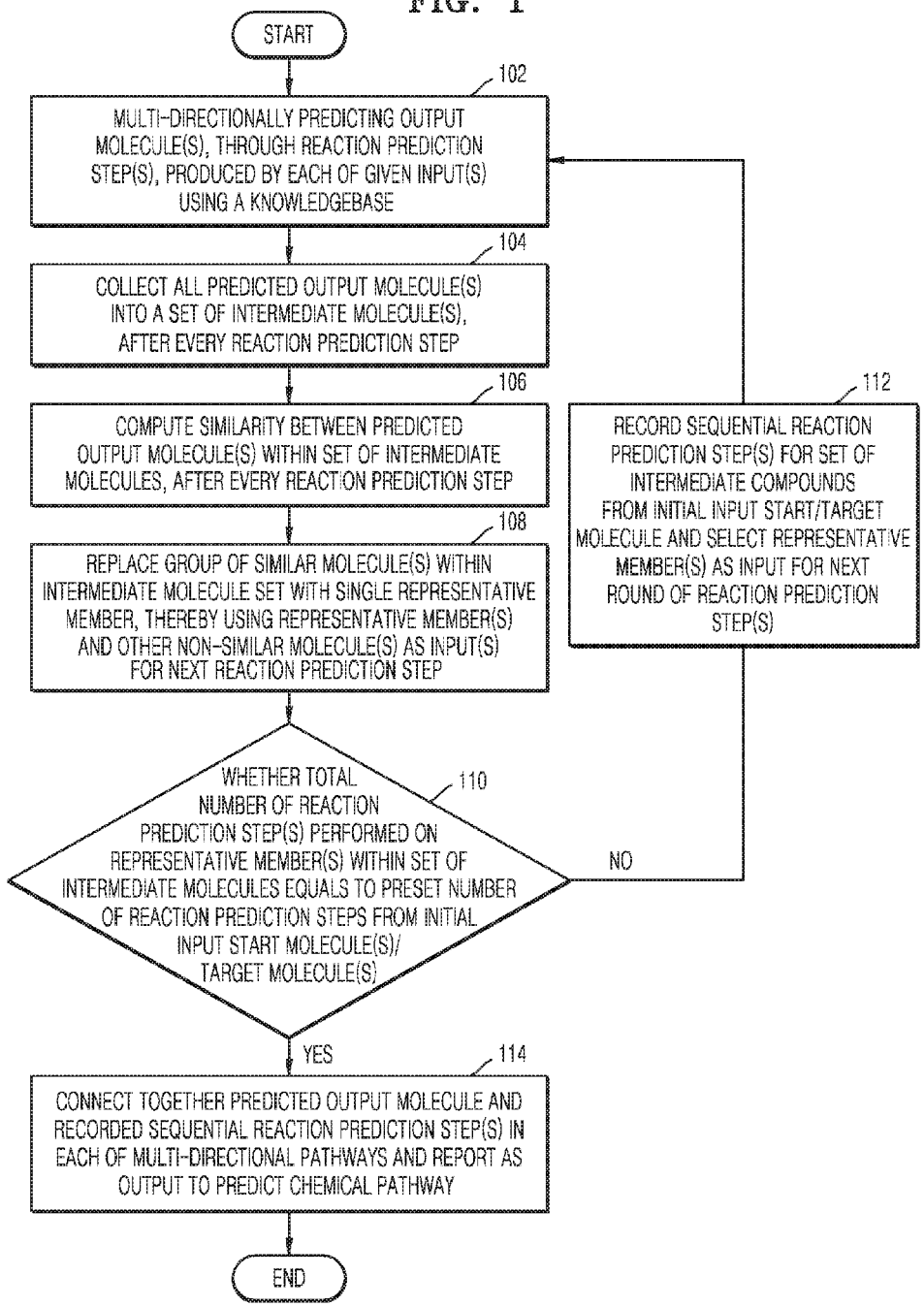
FIG. 1 is a flowchart illustrating a method for performing in silico prediction of a chemical pathway for transforming a start compound to a target compound, according to an embodiment.

FIG. 1 is a flowchart illustrating a method of in silico prediction of a chemical pathway for transforming a start compound to a target compound, according to an embodiment.

The method starts, in operation 102, by performing reaction prediction steps for predicting an output molecule and/or an intermediate in a multi-directional manner for a set of a start compound and a target compound. The reaction prediction steps refer to steps configured to predict reactions occurring during transformation of a start compound to a target compound or transformation of a target compound to a start compound. An output molecule and/or an intermediate subjected to the prediction can be predicted at each of the prediction reaction steps using a knowledgebase.

Figure 2:
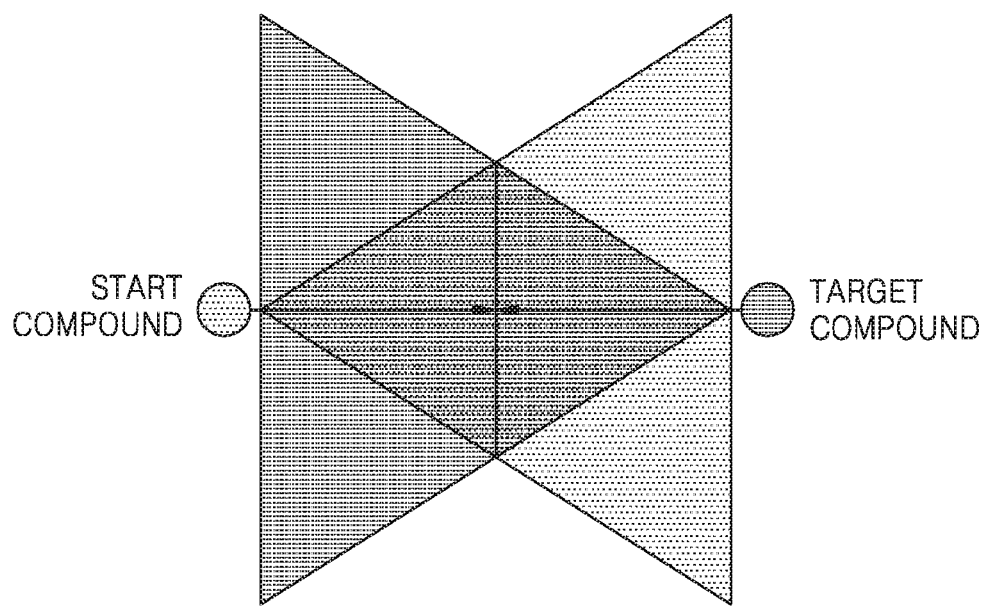
FIG. 2 is a diagram describing prediction of reaction steps for transforming a start compound to a target compound or transforming a target compound to a start compound, and prediction of output molecules, according to an embodiment.

FIG. 2 is a diagram describing the prediction of the reaction steps for transforming a start compound to a target compound or transforming a target compound to a start compound, and the prediction of the output molecules, according to an embodiment.

For example, as shown in FIG. 2, assuming that an input of one start compound and an input of one target compound are each received, two triangles in FIG. 2 each represent a prediction space for predicting transformation from each of the start compound and the target compound. A region overlapped by the triangles represents a chemical pathway that leads from the start compound to the target compound. In some embodiments, the chemical pathway may be predicted based on the reaction prediction steps, and the chemical pathway may be used to predict output molecules that are involved in transformation from the start compound to the target compound or transformation from the target compound to the start compound.

Figure 3:
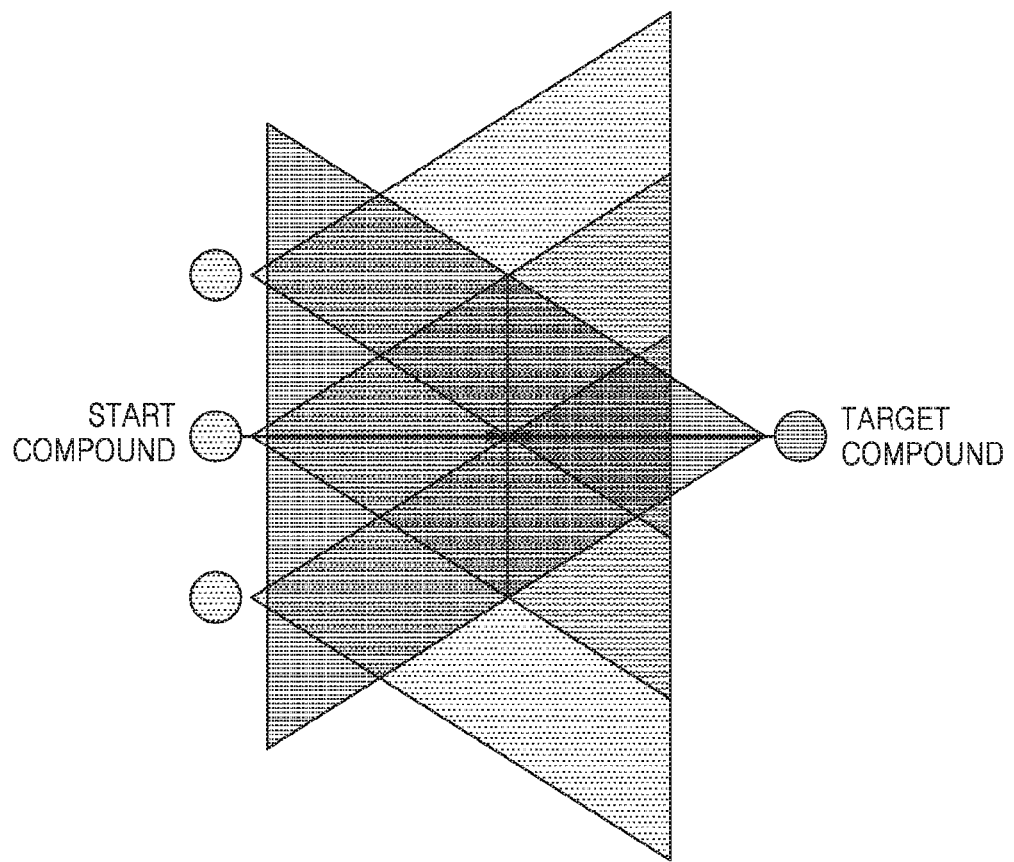
FIG. 3 is a diagram describing prediction of reaction steps for transforming multiple start compounds to a target compound or transforming a target compound to multiple start compounds, and prediction of output molecules, according to an embodiment.

FIG. 3 is a diagram describing prediction of reaction steps for transforming multiple start compounds to a target compound or for transforming a target compound to multiple start compounds, and prediction of output molecules, according to an embodiment.

Referring to FIG. 3, in a different manner from FIG. 2, an input of three start compounds and an input of one target compound may each be received. Triangles may each represent a prediction space to predict transformation started from each of the start compounds and the target compound. According to an embodiment, the chemical pathway may be predicted based on the reaction prediction steps, and in addition, the chemical pathway may be used to predict output molecules that are involved in transformation from the start compounds to the target compound or from the target compound to the start compounds.

The knowledgebase may include a list of reactions, chemical moieties present in the listed reactions, changes taking place in the chemical moieties while the reactions occur, a set of transformation rules governing each of the listed reactions, and a set of transformation rules representing modification of a single list.

The output molecules/intermediates may be predicted at each of the reaction prediction steps by applying a set of transformation rules included in the knowledgebase to the inputs. Afterwards, only the transformation rules leading to modification in the inputs and corresponding reaction prediction steps are recorded. Furthermore, the output molecules produced at a previous reaction prediction step can be used as an input for a next reaction prediction step.

Figure 4:
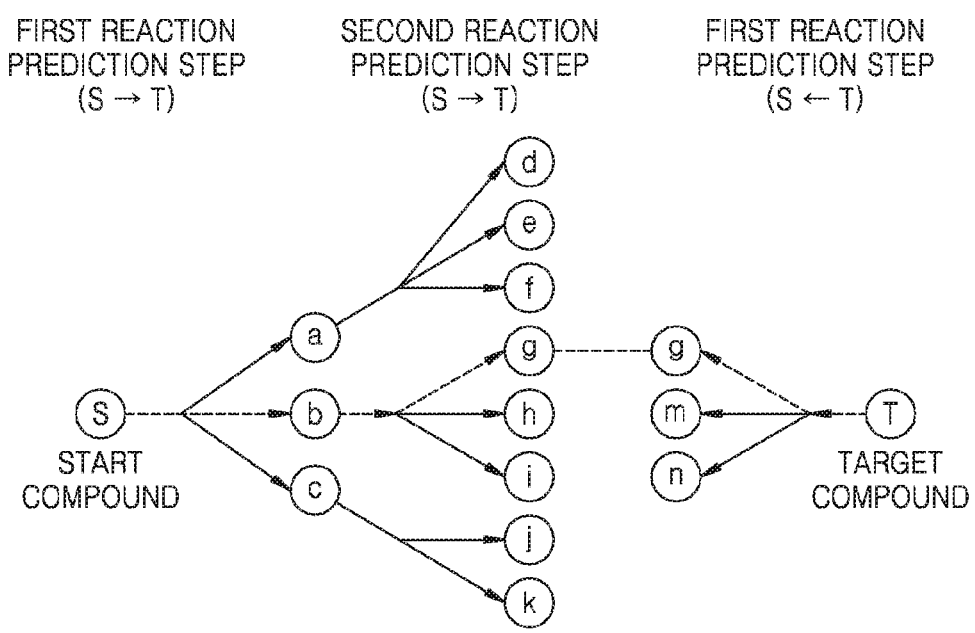
FIG. 4 is a diagram describing an example of multi-directional prediction of reaction steps, according to an embodiment.

FIG. 4 is a diagram describing an example of multi-directional prediction for reaction steps, according to an embodiment.

Referring to FIG. 4, inputs to each of the reaction prediction steps may vary. For example, at an initial reaction prediction step, the start compound or the target compound may be used as an input for producing an output molecule. The output molecule produced at the previous reaction prediction step is referred to as an intermediate, which is used as an input in the next prediction step. An intermediate produced at the final reaction prediction step may be a final output corresponding to the initial input, such as the start compound or the target compound.

In some embodiments, the number of reaction prediction steps associated with the start compound and the target compound may be preset. Here, the preset number of reaction prediction steps associated with the start compound may be identical to or different from the preset number of reaction prediction steps associated with the target compound. In this regard, when the number of reaction prediction steps is preset, the total number of reaction prediction steps to be performed with respect to an initial input (e.g., a start compound and a target compound) may be determined.

Referring to FIG. 1 again, all the predicted output molecules may be collected into a set of intermediate molecules in operation 104. Step 104 may be performed after every reaction prediction step.

In operation 106, similarity (e.g. a similarity score) between the predicted output molecules within the set of intermediate molecules is computed. The computation may be performed after each of the reaction prediction steps or after a preset number of reaction prediction steps. Based on the computed score of the predicted output molecules, groups having similar output molecules may be produced. Furthermore, one output molecule may be selected as a representative member for each of the groups having similar output molecules.

Methods of computing the similarity score for compounds (e.g., output molecules/intermediates) are widely known in the art. For example, various methods, such as chemical fingerprints and sub-structure match are known, but embodiments are not limited thereto. Similarity quantification between two compounds may be performed by computing a similarity metric such as, Tanimoto coefficient and Jaccard score (Willett, 2013; Cereto-Massague et al., 2015), but embodiments are not limited thereto.

Referring to FIG. 4 described above, one of the intermediates (e.g., 'g') produced in the second reaction prediction step for transforming the start compound to the target compound may match with the intermediate (e.g., 'g') produced in the first prediction step for transforming the target compound to the start compound. The same matching configuration may be applied to a scenario where N number of start compounds (wherein N is a natural number) and N number of target compounds are received as an input.

Referring to FIG. 1, in operation 108, each of the groups having similar molecules within the set of the intermediate molecules may be replaced with the single representative member, thereby using the representative member of each of the groups having similar molecules as an input for the next prediction step.

Therefore, to reduce redundancy in pathway prediction computation and computed pathway data, the following processes may be taken into account. That is, as described above, the process of separating the similarly predicted output molecules from the remaining non-similarly predicted output molecules, and the process of selecting the representative member for each of the groups having similar output molecules may be taken into account in terms of reducing computations.

In operation 110, it is analyzed whether a total number of reaction prediction steps performed on the representative member within the set of the intermediate molecules is equal to the preset number of reaction prediction steps from the initial input start compound/target compound. Step 112 or step 114 may be performed depending on the output resulting from the analysis. That is, if the output of the analysis presents that the total number of the reaction predictions performed is equal to the present number of reaction prediction steps from the initial input start compound/target compound, step 114 commences. In some embodiments, if the output of the analysis presents that the total number of the reaction predictions performed is not equal to the present number of reaction prediction steps from the initial input start compound/target compound, step 112 commences and steps 102 to 108 are repeated in succession again. Here, the input for step 102 may include a representative member of a group.

In operation 112, sequential reaction prediction steps for the set of the intermediate compound produced from the initial input start/target compounds are recorded, and the representative member is selected as the input for the next reaction prediction step.

In step 114, the start compound, the target compound, the multi-directionally predicted output molecules, and the sequence of the reaction prediction steps are connected with each other to predict chemical pathways.

The predicted chemical pathways include sequential arrangement of a plurality of chemical reactions (reaction prediction steps) governed by the transformation rules.

In FIG. 4, the similarity between the predicted output molecules within the set of intermediate molecules may be computed after the performance of the preset number of reaction prediction steps. In some embodiments, the preset number is 2 steps with respect to the reaction prediction steps from the start compound to the target compound, whereas the preset number is 1 step with respect to the reaction prediction steps from the target compound to the start compound. For example, a similar molecule 'g' is found during this process. The reaction prediction steps starting from a start compound 'S', including intermediate molecules 'b' and 'g', and ending at a target compound 'T' may be connected with the transformation rules governing those reaction prediction steps. That is, to predict a chemical pathway (e.g., S→b→g→T) transforming the start compound to the target compound, the reaction prediction steps and their corresponding transformation rules may be connected. In this regard, a necessary pathway may be excluded, and accordingly, the computation may be reduced in terms of the pathway prediction computation and computed pathway data.

The number of predictions may grow exponentially with the length of simulation. However, according to an embodiment, the predicted data may be significantly reduced. In some embodiments, one-way prediction in four steps may be transformed into bi-direction prediction in two steps. For example, a typical simulation with a rule library of 100 or less rules may give 25 predictions on average for each of the input molecules. Therefore, regarding simulation associated with length n (wherein n is a natural number), $25^n$ predictions may be performed.

When n denotes the length of simulation, there may be $25^n$ predictions.

For example, from one-direction simulation of length 4, 390,625 ($=25^4$) reactions may be predicted. In some embodiments, from bi-directional simulation of length 2+2, 1,250 ($=25^2+25^2$) reactions may be predicted. Therefore, as described here, a many-fold reduction in the number of predicted reactions may be achieved using the bi-directional simulation started from each of the start compound and the target compound.

Referring to FIG. 2, when assuming that each of the intermediate molecules is predicted through bottom-up prediction in the simulation for predicting the target compound from the start compound, the simulation may result in about $625(=25^2)$ pathways. In practice, the number of simulations may be less than the overlap between the intermediates (i.e., similarity), resulting in fewer pathways to be assessed.

Referring to FIG. 3, the simulation may be started from both directions, starting from the multiple start compounds and one target compound. Then, the predicted reactions are linked to form pathways. The amount of data produced herein depends on the number of start (or target) compounds used herein. The reactions predicted through bi-directional simulation may result in 63,125 reactions. Regarding the production of data and prediction of pathways, this result may bring 84% computation reduction.

In operation 114 described earlier, after predicting a set of chemical pathways, the predicted chemical pathways are verified based on feasibility, kinetics, and/or abundance of intermediates produced in the chemical pathways.

The finally predicted chemical pathways may then be selected from the chemical pathways that are classified before.

Figure 5:
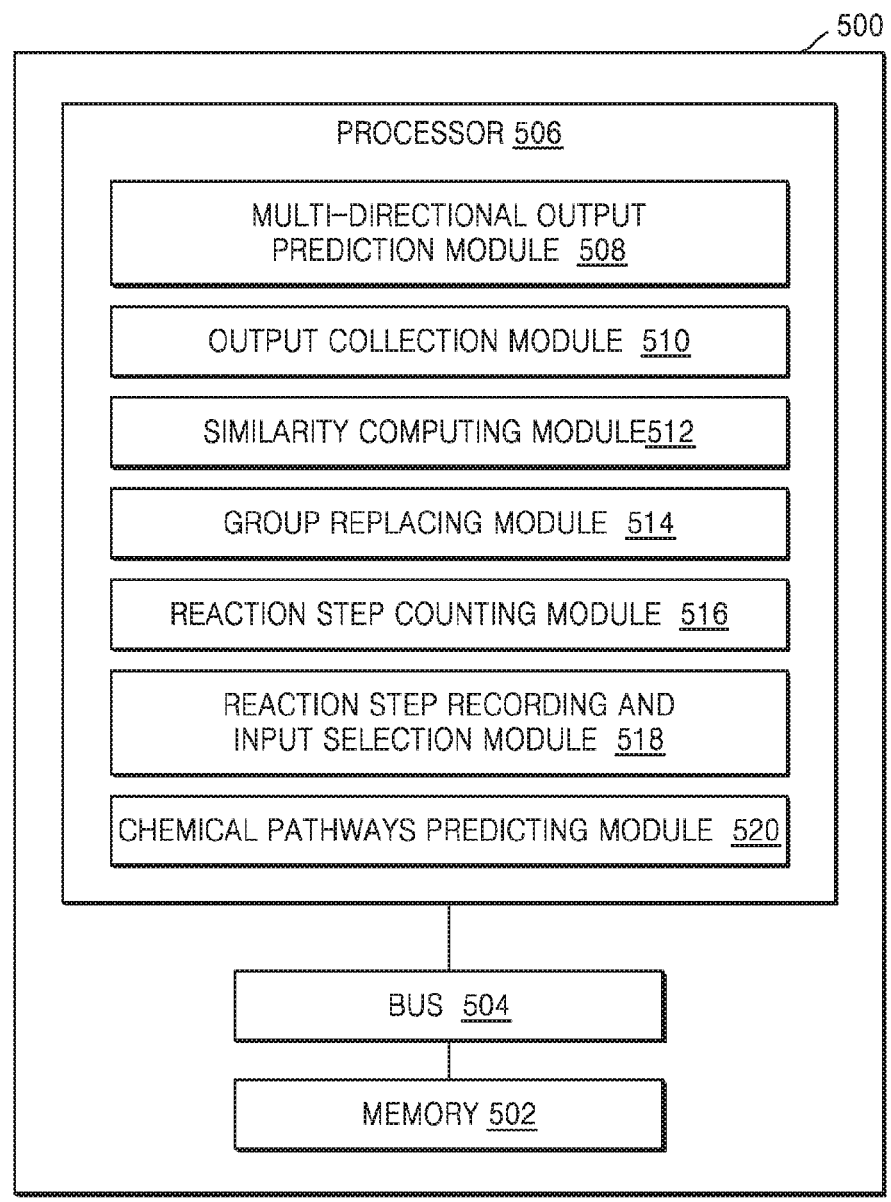
FIG. 5 is a block diagram illustrating a device for in silico prediction of a chemical pathway for transforming a start compound to a target compound, according to an embodiment.

FIG. 5 is a block diagram that illustrates a device for in silico prediction of a chemical pathway for transforming a start compound to a target compound, according to an embodiment.

A device 500 includes a processor 506 and a memory 502 coupled to the processor 506 via a bus 504.

The processor 506 may be implemented by any type of computational circuit, such as a microprocessor, a microcontroller, a complex instruction set computing (CISC) microprocessor, a reduced instruction set computing (RISC) microprocessor, a very long instruction word (VLIVV) microprocessor, an explicitly parallel instruction computing (EPIC) microprocessor, a digital signal processor (DSP), or any other type of processing circuit, or a combination thereof.

The processor 506 may include a multi-directional output prediction module 508, an output collection module 510, a similarity computing module 512, a group replacing module 514, a reaction step counting module 516, a reaction step recording and input selection module 518, and a chemical pathways predicting module 520.

The memory 502 may include executable programs configured to be performed by each component of the processor 506.

Computer memory elements may include an appropriate memory device for storing data and executable programs, and examples of the memory device include read only memory (ROM), random access memory (RAM), erasable programmable read only memory (EPROM), electrically erasable programmable read only memory (EEPROM), a hard drive, and a removable media drive for handling a memory card. In an embodiment, a prediction method may be implemented in conjunction with program modules, including functions, procedures, data structures, and application programs, for performing tasks, or defining abstract data types or low-level hardware contexts. Executable program stored on any of the above-mentioned storage media may be executable by the processor 506.

The multi-directional output prediction module 508 instructs the processor 506 to perform operation 102 of FIG. 1.

The output collection module 510 instructs the processor 506 to perform operation 104 of FIG. 1.

The similarity computing module instructs the processor 506 to perform operation 106 of FIG. 1.

The group replacing module 514 instructs the processor 506 to perform operation 108 of FIG. 1.

The reaction counting module 516 instructs the processor 506 to perform operation 110 of FIG. 1.

The reaction step recording and input selection module 518 instructs the processor 506 to perform operation 112 of FIG. 1.

The chemical pathway predicting module 520 instructs the processor 506 to perform operation 114 of FIG. 1.

In some embodiments, the method of in silico prediction of chemical pathways for transforming the start compound to the target compound may be performed by a directed search for identifying a sequence of the transformations taking place in the start compound or intermediates on application of provided transformation rules.

When the transformation rules are executed, the sequential conversion in chemical moiety of functional groups of the start compound or intermediate may be used. The sequence of the transformation associated with the transformation rules causing modification in the functional group of the start compound and/or the intermediate may be recorded and analyzed using the transformation rule matrix.

The chemical moiety is a part of a molecule, which may include either a whole functional group or a part of a functional group. For example, an ester group (RCOOR') has an ester functional group (COOR) and is composed of an alkoxy moiety (—OR') and an acyl moiety (RCO—). In some embodiments, the chemical moiety may include a functional group including a chemical moiety. The functional group used herein refers to a specific group of atoms or bonds within molecules that are responsible for the characteristic chemical reactions of the molecules.

The molecular transformation may include transformation of a chemical moiety residing on a molecule, and may include modification of at least one of chemical bonds, bond rearrangements, and chemical states, which undergo a reaction process.

Figure 6:
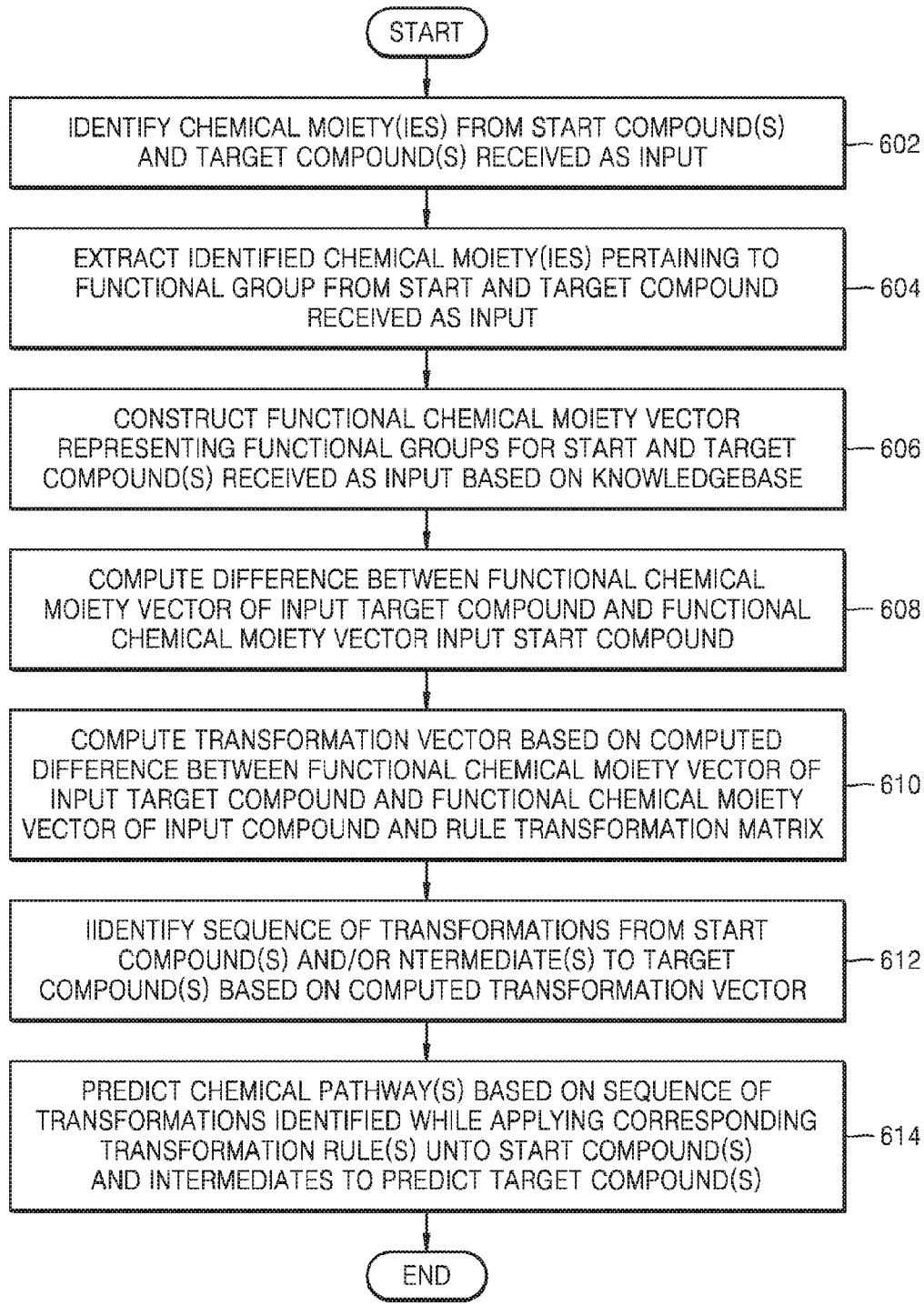
FIG. 6 is a schematic flowchart illustrating a method for in silico prediction of a chemical pathway for transforming a start compound to a target compound, according to another embodiment.

FIG. 6 is a schematic flowchart illustrating the method for in silico prediction of the chemical pathway for transforming the start compound to the target compound, according to another embodiment.

In operation 602, the chemical moieties residing on the start compound and the target compound are identified. Such identification of the chemical moieties may be performed by methods known in the art. The identification of the chemical moieties may be performed with reference to the knowledgebase about a pair of the one start compound the one target compound. In some embodiments, when the initial input includes a plurality of start compounds or target compounds, one or more pairs of the start compound and the target compound may be included. In such cases, one pair of the one start compound and the one target compound is processed for identification of the chemical moieties.

For example, the input received may include ethanol as a start compound, and ethanoic acid (acetic acid) and ethanoyl coenzyme A (acetyl CoA) as two target compounds. Here, two pairs may include: (a) a pair of ethanol and acetic acid and (b) a pair of ethanol and acetyl CoA. The first pair (a) of ethanol and acetic acid is processed to identify the presence of chemical moieties of a CH group, a hydroxyl (—OH) group, and a carboxylate (C(=O)OH) group. The second pair (b) of ethanol and acetyl CoA is processed to identify the presence of chemical moieties of a CH group, a hydroxyl (OH) group, and a CoA.

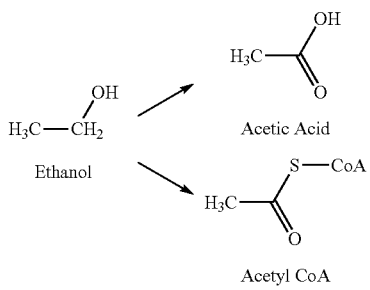

The identified chemical moieties pertaining to a functional group from each pair of the start compound and the target compound are extracted in operation 604. The extracted chemical moieties may be at least one functional group in one of the start compound, the intermediate molecule, and the target compound. By referring to the pair (a) of ethanol and acetic acid as described above, the chemical moieties pertaining to the functional group of the CH group, the —OH group, and the C(=O)OH group are extracted.

A functional chemical moiety vector representing functional groups of the start and target compounds received as inputs is constructed based on the knowledgebase in operation 606. For example, a functional chemical moiety vector constructed for the extracted chemical moieties pertaining to the functional groups [i.e., the CH group, the —OH group, and the C(=O)OH group] may be represented as shown in Table 1.

TABLE 1

| Functional chemical moieties | Start compound (ethanol) | Target compound (acetyl CoA) |
|---|---|---|
| C—H | 5 | 3 |
| C—OH | 1 | 0 |
| C(=O)OH | 0 | 1 |

A difference between the functional chemical moiety vector of the input target compound and the functional chemical moiety vector of the input start compound is computed in operation 608.

| Chemical moieties | Target compound (acetic acid) | | Start compound (ethanol) | | Difference between functional chemical moiety vector |
|---|---|---|---|---|---|
| C—H | 3 | − | 5 | = | −2 |
| C—OH | 1 | | 1 | | 0 |
| C(=O)OH | 1 | | 0 | | 1 |

A transformation vector is computed in operation 610 based on the computed difference between the functional chemical moiety vector of the input target compound and the functional chemical moiety vector of the input start compound and the transformation rule matrix. The transformation rule matrix includes a plurality of columns and a plurality of rows, wherein the columns each represent a transformation rule and the rows each represent a functional group of the identified chemical moiety.

Therefore, the number of columns in the matrix is directly proportional to the number of transformation rules present in the knowledgebase or to the number of transformation rules selected to be used in an embodiment.

The intermediate may be produced after application of a set of transformation rules, which are obtained from the knowledgebase or the transformation rule matrix, with respect to the initially input start compound. The transformation rule matrix is produced based on the effect of transformation rules on the input, and then, relevant transformation rules and association reaction steps are identified, thereby forming the first step in prediction of the reaction steps. Furthermore, the intermediate produced at a previous chemical reaction prediction step may be used as an input for the next chemical reaction prediction step. The process may be repeated until the target compound is obtained.

FIG. 7 is diagram that illustrates an equation using the transformation rule matrix, according to an embodiment.

Referring to FIG. 7, when the difference between the functional chemical moiety vectors of the input is computed, a transformation rule matrix T including rows corresponding to the identified functional groups and columns corresponding to the transformation rules is constructed. The transformation rule matrix may be produced based on predefined rules of: (a) negative entry representing the transformation rules acted on the identified chemical moiety leading to either deletion or modification of the identified chemical moiety; (b) positive entry representing the transformation rules acted to lead to the formation of a new chemical moiety; and (c) zero entry meaning no effect brought upon the identified chemical moiety by application of the transformation rules.

The difference in the functional groups between the start and target molecules is identified, and then, the identification is recorded as vector D. To identify a set of coefficients corresponding to the transformation rules, the following equation may be used:

$$T \times C = D \quad \text{[Equation 1]}$$

wherein C denotes a coefficient vector.

Such an equation above may be solved using methods for solving linear equations. In some embodiments, a graph traversal method is used to identify rule paths needed to convert the functional groups of the start molecule to the functional groups of the target molecule. In some embodiments, a directed search method based on the knowledge-base including 4 transformation rules while having functional groups of the '—CH' group and the 'C(=O)SCoA' group in the start and target compounds is shown in FIG. 8.

FIG. 8 is a diagram describing a way to obtain coefficient vector C using the equation of FIG. 7. Referring to FIG. 8, the transformation rules and modification in chemical moieties on the input are as follows:

R1: C—H→C—OH 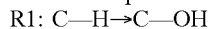
R2: C—OH→C=O 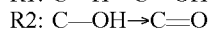
R3: C=O→C(=O)OH 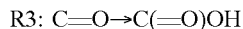
R4: C=O→C(=O)SCoA. 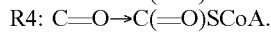

To convert C—H to C(=O)OH, the method predicts use of Rules 1, 2, and 3. Furthermore, the transformation rules needed for a potential start compound and a modification thereof may be identified.

Based on the computed coefficient vector, the sequence of transformations from the start compounds or the intermediates to the target compounds may be identified in operation 612 of FIG. 6. Referring to an example of FIG. 8, the sequence of transformations and relevant transformation rules are as follows:

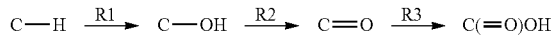

To predict the target compound, a chemical pathway is predicted based on the sequence of the transformations identified while applying corresponding transformation rules to the start compound and the intermediate in operation 614.

As described above, the chemical pathway may include sequential arrangement of a plurality of chemical reactions governed by transformation rules.

The predicted chemical pathway may be refined to reduce the data to be assessed for finding out the most efficient chemical pathway for bringing out transformation or any other user requirement. The refinement may enable users to select the most appropriate pathway out of all the predicted or received chemical pathways for the transformation.

Figure 9:
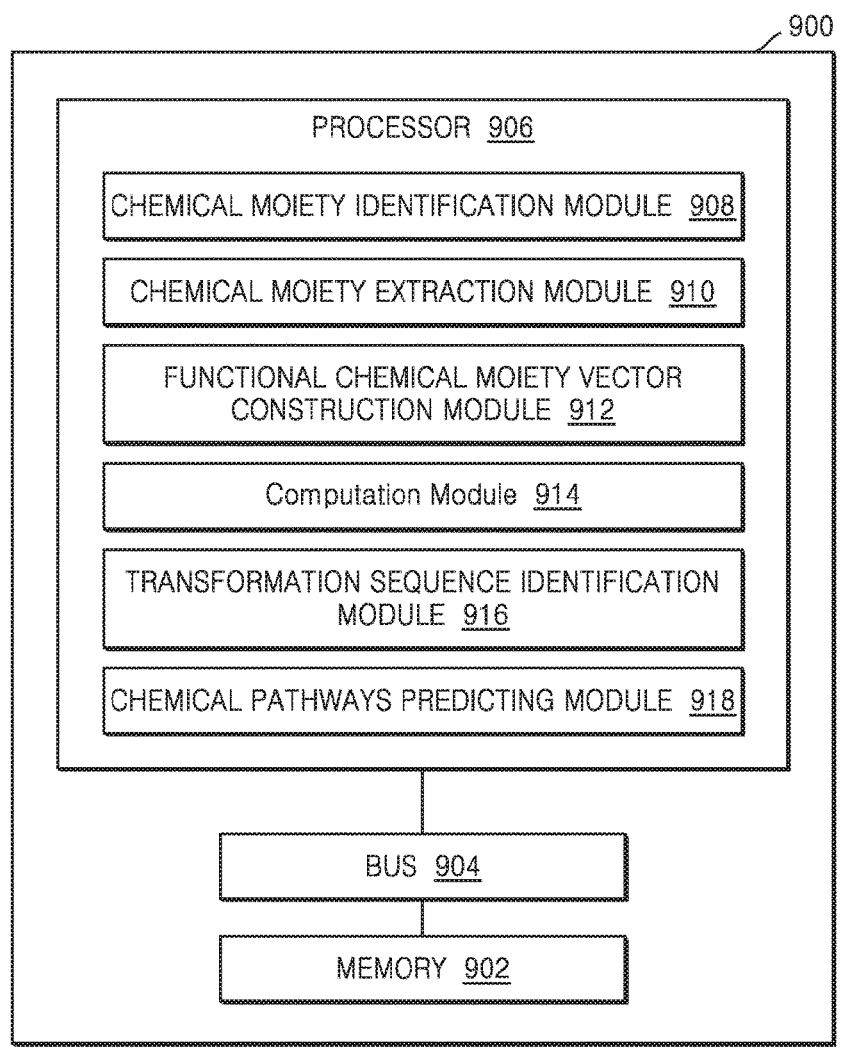
FIG. 9 is a block diagram illustrating a device for in silico prediction of a chemical pathway for transforming a start compound to a target compound, according to another embodiment.

FIG. 9 is a block diagram that illustrates a device for in silico prediction of a chemical pathway for transforming a start compound to a target compound, according to another embodiment.

A device 900 includes a processor 906 and a memory 902 coupled to the processor 906 via a bus 904.

The processor 906 may be implemented by any type of computational circuit, such as a microprocessor, a microcontroller, a CISC microprocessor, a RISC microprocessor, a VLIW microprocessor, an EPIC microprocessor, a DSP, or any other type of processing circuit, or a combination thereof.

The processor 906 may include a chemical moiety identification module 908, a chemical moiety extraction module 910, a functional chemical moiety vector construction module 912, a computation module 914, a transformation sequence identification module 916, and a chemical pathways predicting module 918.

The memory 902 may include executable programs configured to be performed by each component of the processor 906.

Computer memory elements may include an appropriate memory device for storing data and executable programs, and examples of the memory device include ROM, RAM, EPROM, EEPROM, a hard drive, and a removable media drive for handling a memory card. In an embodiment, a prediction method may be implemented in conjunction with program modules, including functions, procedures, data structures, and application programs, for performing tasks, or defining abstract data types or low-level hardware contexts. Executable programs stored on any of the above-mentioned storage media may be executable by the processor 906.

The chemical moiety identification module 908 instructs the processor 906 to perform operation 602 of FIG. 6.

The chemical moiety extraction module 910 instructs the processor 906 to perform operation 604 of FIG. 6.

The functional chemical moiety vector construction module 912 instructs the processor 906 to perform operation 606 of FIG. 6.

The computation module 914 instructs the processor 906 to perform operations 608 and 610 of FIG. 6.

The transformation sequence identification module 916 instructs the processor 906 to perform operation 612 of FIG. 6.

The chemical pathways predicting module 918 instructs the processor 906 to perform operation 614 of FIG. 6.

Figure 10:
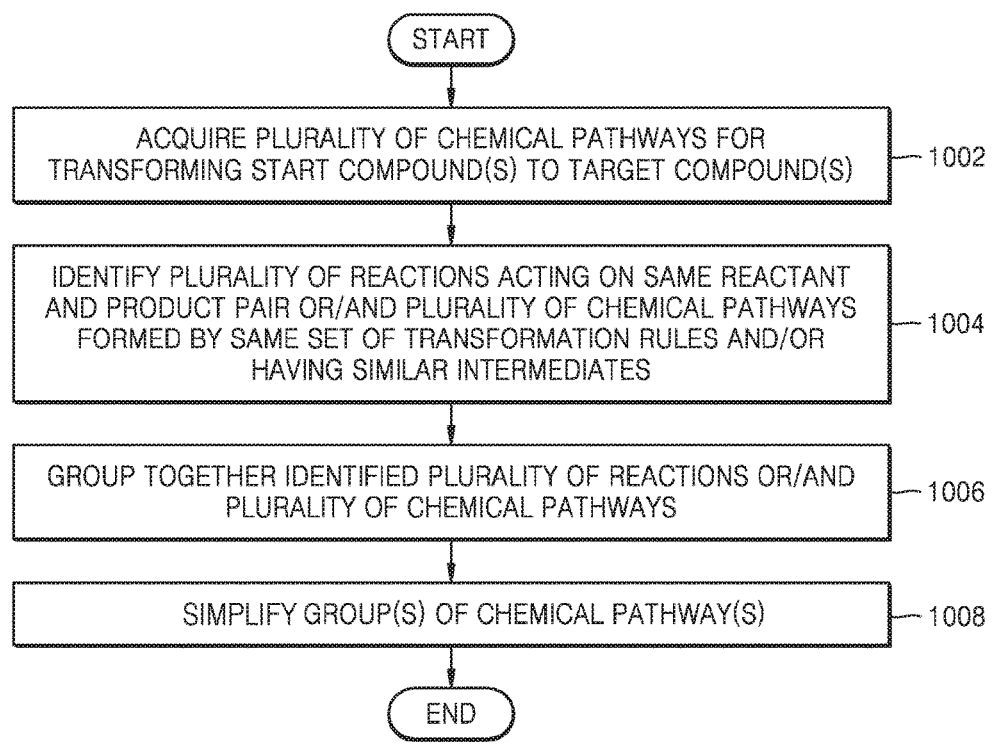
FIG. 10 is a schematic flowchart illustrating simplification of a chemical pathway for transforming a start compound to a target compound, according to another embodiment.

In some embodiments, a method of simplification of chemical pathways predicted or obtained for transforming the start compound to the target compound is provided. To reduce redundancy in the total amount of reactions to be assessed, the simplification may be performed by grouping at a level of the chemical reactions and the chemical pathways. The simplification may be applied after the disclosed methods of the in silico prediction of chemical pathways for transforming start compounds to target compounds or on a set of chemical pathways provided by some other methods/outside source to refine the chemical pathways FIG. 10 is a schematic flowchart illustrating simplification of a chemical pathway for transforming a start compound to a target compound, according to another embodiment.

A plurality of chemical pathways for transforming the start compound to a target compound may be obtained in operation 1002. The chemical pathways include a sequential arrangement of a plurality of chemical reactions governed by transformation rules received from or based on a knowledgebase. The chemical pathways obtained therefrom may be edited by the methods of in silico prediction of the chemical pathways for transforming the start compound to a target compound according to the methods of FIGS. 1 and 6 or other methods.

The knowledgebase may include a list of reactions, chemical moieties present in the listed reactions, changes taking place in the chemical moieties while the reactions occur, a set of transformation rules governing each of the listed reactions, and a set of transformation rules representing modification of a single list.

The obtained chemical pathway is analyzed to identify (a) to (c) below in operation 1004:

(a) a chemical reaction acting on a pair of the same reactant and product, where a plurality of the reactions herein, can be predicted/produced using different rules present in the knowledgebase;

(b) a chemical pathway for the start compound to the target compound, wherein the chemical pathway is formed by a set of the transformation rules; and (c) a chemical pathway having similar intermediates for the start compound to the target compound.

The chemical reactions analyzed herein are reactions present in the obtained chemical pathways. In operation 1002, chemical reactions that are different from each other and act on the same reactant to yield the same product are detected. Therefore, such chemical reactions can replace each other in the chemical pathways, and furthermore, the most efficient chemical reaction, other than the chemical reactions above, can be chosen to be used in next steps.

When such chemical reactions or chemical pathways are identified, it becomes easy to remove a cycle or futile transformation present in the chemical pathways.

The grouping is performed at levels of chemical reactions or chemical pathway in operation 1006. The identified (a) chemical reactions acting on the same reactant and product pair may be grouped together; the identified (b) chemical pathways formed by the set of the transformation rules or the identified (c) plurality of the chemical pathways having similar intermediates may be grouped together.

The reaction grouping deals with grouping of chemical reactions that have the same reactant and product pair, and may be predicted using different rules. Such a pair may offer a same pathway using different chemistries or enzymes.

Furthermore, based on physio-chemical characteristics or statistical properties, one chemical reaction from each group may be selected as a representative. In this regard, the representative chemical reaction may be used to replace the other chemical reactions of the same group in the chemical pathways. Here, the other chemical reactions may be less efficient. Therefore, such a method may impart desired efficiency in the chemical pathways, and may significantly reduce redundancy in the total amount of reactions to be assessed. Due to merging such grouped chemical reactions and replacing them with a single representative reaction, the data to be assessed may be reduced by about 30% or more, as shown in Table 2.

For example, in the case of the reaction level group after the identification operation (operation 1004), it is found that there are 5 different chemical reactions which convert A to B, 1 chemical reaction which converts reactant B to product C, and 7 chemical reactions which convert C to D. Then, three groups of chemical reactions are formed, wherein the first group includes 5 chemical reactions which convert A to B, the second group includes 1 chemical reaction which converts B to C, and the third group includes 7 chemical reactions which convert C to D.

Figure 11A:
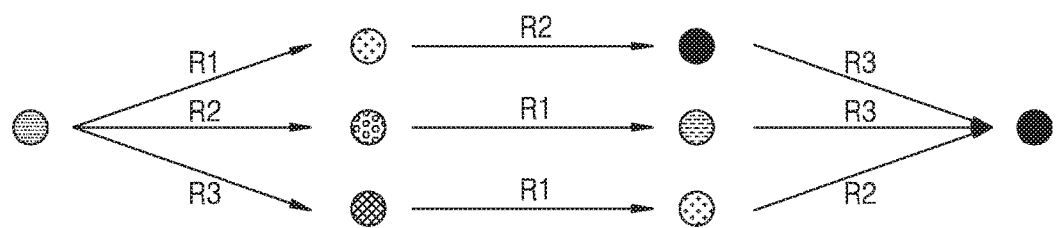
FIG. 11A is a diagram describing grouping at a chemical pathway level, according to another embodiment.

FIG. 11A is a diagram describing grouping at a chemical pathway level, according to another embodiment.

Grouping at the chemical pathway level may be illustrated as shown in FIG. 11A. All the three pathways lead from the same start compound to the target compound. Different intermediates may be obtained in each pathway, but all the three chemical pathways are grouped together. These chemical pathways will be simplified into a set for pathway assessment in operation 1008.

Figure 11B:
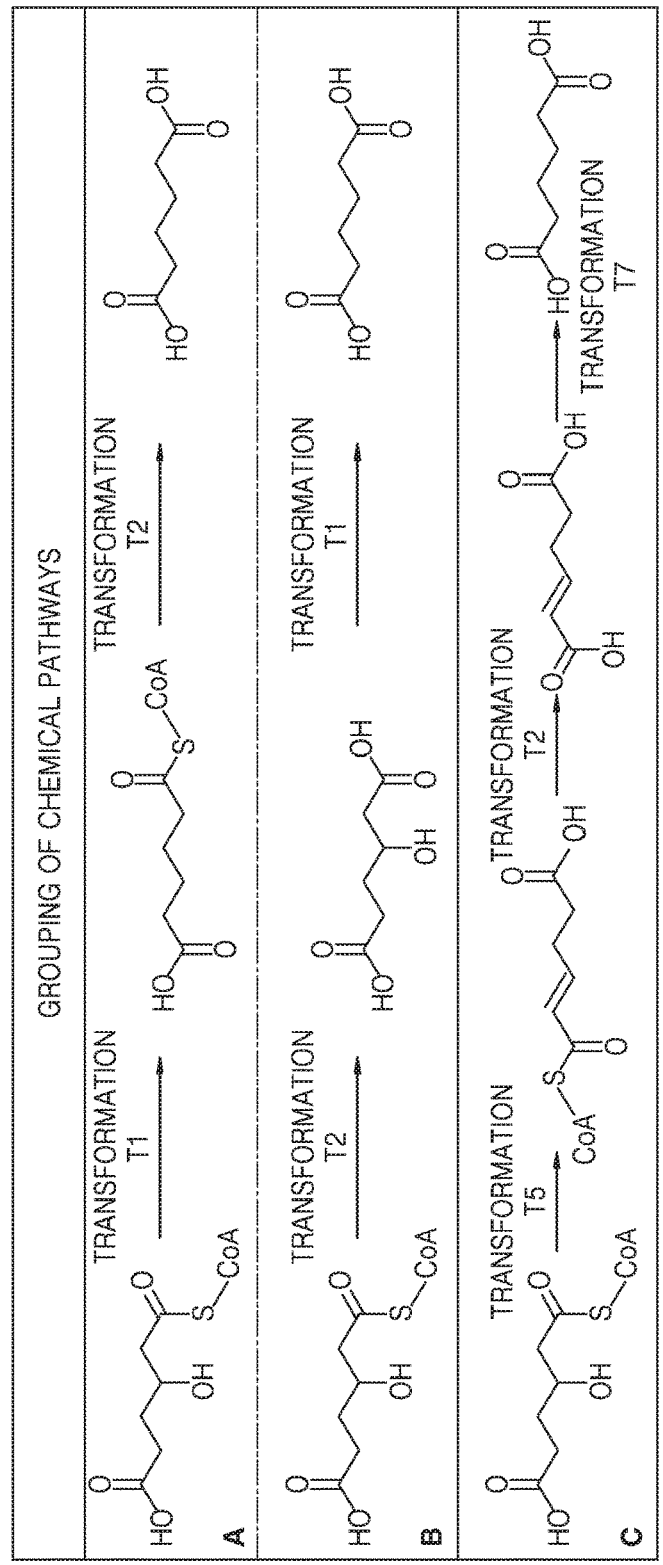
FIG. 11B is a diagram describing grouping at a chemical pathway level, according to another embodiment.

FIG. 11B is a diagram describing grouping at a chemical pathway level, according to another embodiment. Pathways A, B, and C have the same start and end compounds and use the same transformation rules. However, the pathways A and B have similar set of transformation rules, in a different manner from pathway C. Therefore, two groups may be formed herein, wherein the first group includes A and B, and the second group only includes C.

The groups of the chemical pathways for transforming the start compounds to the target compounds are simplified in operation 1008. This operation brings about the pathway simplification in groups of the chemical pathways. These pathways involve the same chemistries/transformations happening in different order. As the order does not matter to the outcome of the pathway, these pathways can all be assessed as a single group.

Figure 11C:
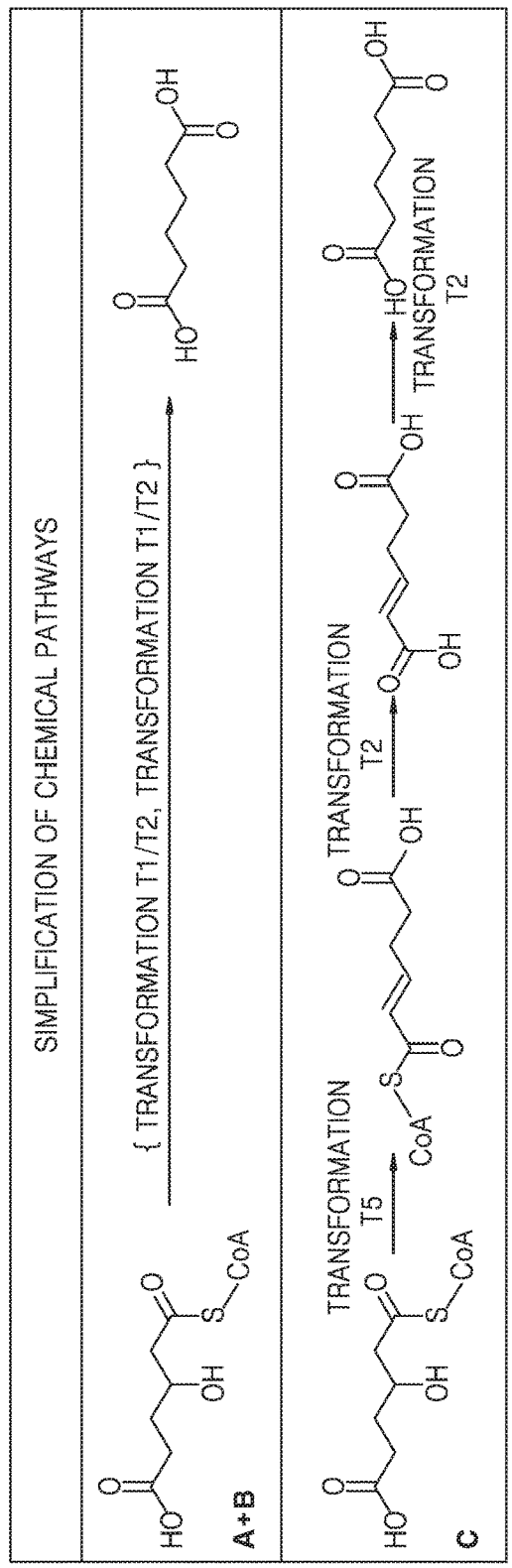
FIG. 11C is a diagram describing simplification of the groupings at the chemical pathways, according to another embodiment.

FIG. 11C is a diagram describing simplification of the groupings at the chemical pathways, according to another embodiment. A first group may be simplified as A+B to represent one chemical pathway. Since a second group contains only one pathway, hence no further simplification is performed.

The simplification of the chemical pathways results in over 80% reduction in amount of data to be assessed.

TABLE 2

| Refinement methods | Reduction in number of pathways (%) | |
|---|---|---|
| | Putrescine | Adipic acid |
| Cycle removal | 12.71 | 12.93 |
| Simplification | 81.37 | 85.41 |
| Combination of all methods | 88.41 | 92.72 |

In Table 2, the influence of the chemical pathway assessment methods are shown with respect to the predicted number of pathways. As shown in Table 2, the amount of data to be assessed may be generally reduced by about 90% according an embodiment.

The simplified groups of chemical pathways formed in operation 1008 may be assessed based on predefined parameters. The predefined parameters for assessing the groups of chemical pathways include physio-chemical and statistical properties, but embodiments are not limited thereto. To further refine the selection criteria, a user may use preferred parameters.

To perform simplification of the chemical pathways in a more efficient manner, the cycle of the intermediates or transformations present in each of the chemical pathways may be removed in operation 1006. When the transformation rules of the same set, the reactions acting on the same predicted/obtained reactant and product pair, or the plurality of the chemical pathways are identified in operation 1004, it becomes easy to remove the cycle.

When the cycle contains the same molecule/intermediate appearing two or more times, the cycle of the intermediates is formed in the chemical pathway. The chemical pathway having such a cycle is not necessary as it includes redundant transformations. The removal of the cycle of the intermediates can result in cleaning of about 5% of the pathway.

The chemical pathway may include the cycle of transformation, which may be referred to as a futile transformation pair that results in no net effect on the outcome of the pathway. The transformation rules may transform a functional group, and later the reverse of the transformation rules may transform back to the original form thereof. Such transformation pairs are futile, and pathways involving the transformation pairs are discarded.

Figure 12A:
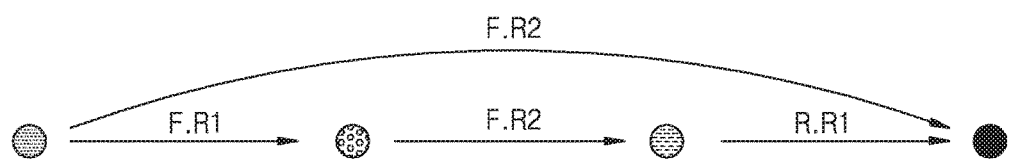
FIG. 12A is a diagram describing a futile transformation pair, according to another embodiment.

FIG. 12A is a diagram describing a futile transformation pair, according to another embodiment. Referring to FIG. 12A, application of forward (F.R1) and reverse (R.R1) of rule R1 has no net impact on the pathway. A pathway based only on forward of rule R2 does the same net transformation.

Figure 12B:
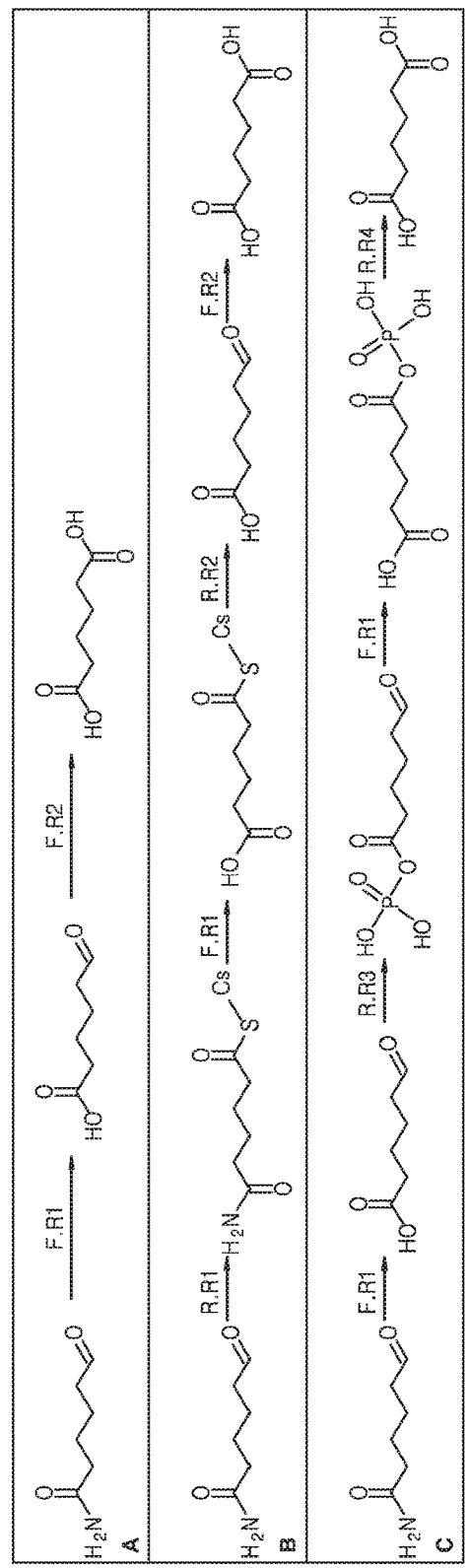
FIG. 12B is a diagram describing an example of chemical pathways having futile transformations, according to another embodiment.

FIG. 12B is a diagram describing an example of chemical pathways having futile transformations, according to another embodiment. To identify such pathways, all pathways between the same start and end compounds are analyzed. Pathways A, B, and C may have the same start and end compounds. Each pathway in this group is represented by the rule set involved in the pathway. The pathways B and C involve application of both forward (F) and reverse (R) of rules R1 and R2, respectively. Application of these rules results in no net effect on the outcome of pathways. Removal of futile transformations results in a clean-up of over 10%.

Figure 13:
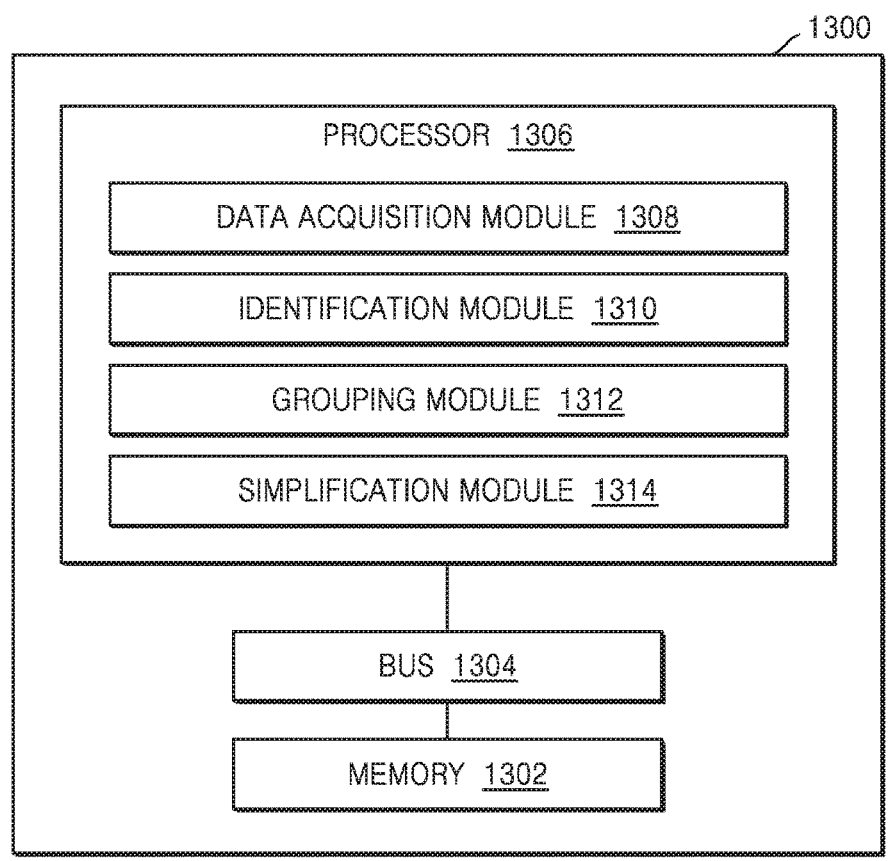
FIG. 13 is a block diagram illustrating a device for simplifaction of a chemical pathway for transforming a start compound to a target compound, according to another embodiment.

FIG. 13 is a block diagram that illustrates a device for simplification of a chemical pathway for transforming a start compound to a target compound, according to another embodiment.

A device 1300 includes a processor 1306 and a memory 1302 coupled to the processor 1306 via a bus 1304.

The processor 1306 may be implemented by any type of computational circuit, such as a microprocessor, a microcontroller, a CISC microprocessor, a RISC microprocessor, a VLIW microprocessor, an EPIC microprocessor, a DSP, or any other type of processing circuit, or a combination thereof.

The processor 1306 may include a data acquisition module 1308, an identification module 1310, a grouping module 1312, and a simplification module 1314.

The memory 1302 may include executable programs configured to be performed by each component of the processor 1306.

Computer memory elements may include an appropriate memory device for storing data and executable programs, and examples of the memory device include ROM, RAM, EPROM, EEPROM, a hard drive, a removable media drive for handling a memory card. In an embodiment, a prediction method may be implemented in conjunction with program modules, including functions, procedures, data structures, and application programs, for performing tasks, or defining abstract data types or low-level hardware contexts. Executable programs stored on any of the above-mentioned storage media may be executable by the processor 1306.

The data acquisition module 1308 instructs the processor 1306 to perform operation 1002 of FIG. 10.

The identification module 1310 instructs the processor 1306 to perform operation 1004 of FIG. 10.

The grouping module 1312 instructs the processor 1306 to perform operation 1006 of FIG. 10.

The simplification module 1314 instructs the processor 1306 to perform operation 1008 of FIG. 10.

Figure 14:
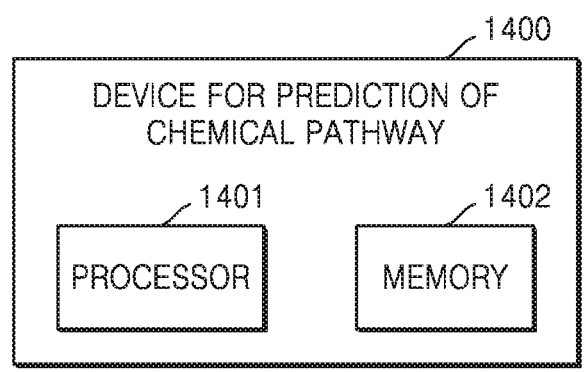
FIG. 14 is a block diagram illustrating a device for prediction of a chemical pathway, according to another embodiment.

FIG. 14 is a block diagram that illustrates a device for prediction of a chemical pathway, according to another embodiment. Referring to FIG. 14, a chemical pathway prediction device 1400 includes a processor 1401 and a memory 402.

The chemical pathway prediction device 1400 may correspond to the device 500 of FIG. 5, the device 900 of FIG. 9, or the device 1300 of FIG. 13. Therefore, the processor 1401 may correspond to the device 506 of FIG. 5, the device 906 of FIG. 9, or the device 1306 of FIG. 13. Therefore, even if the description thereof is omitted, operations and functions that can be performed by the device 500, 900, or 1300 and the processor 506, 906, or 1306 may be performed by the device 1400 and the processor 1401 of FIG. 14.

The processor 1401 predicts an output molecule produced in reaction prediction steps started from each of the start compound and the target compound. In addition, the processor 1401 is configured to obtain one or more output molecules having similarity between the output molecules predicted from the start compound and the output molecules predicted from target compound. Furthermore, the processor 1401 predicts a chemical pathway by associating the order of the reaction prediction steps proceeded with the one or more output molecules that have similarity between the output molecules predicted from the start compound and the output molecules predicted from the target compound.

The memory 1402 may include executable programs configured to be performed by each component of the processor 1401.

Figure 15:
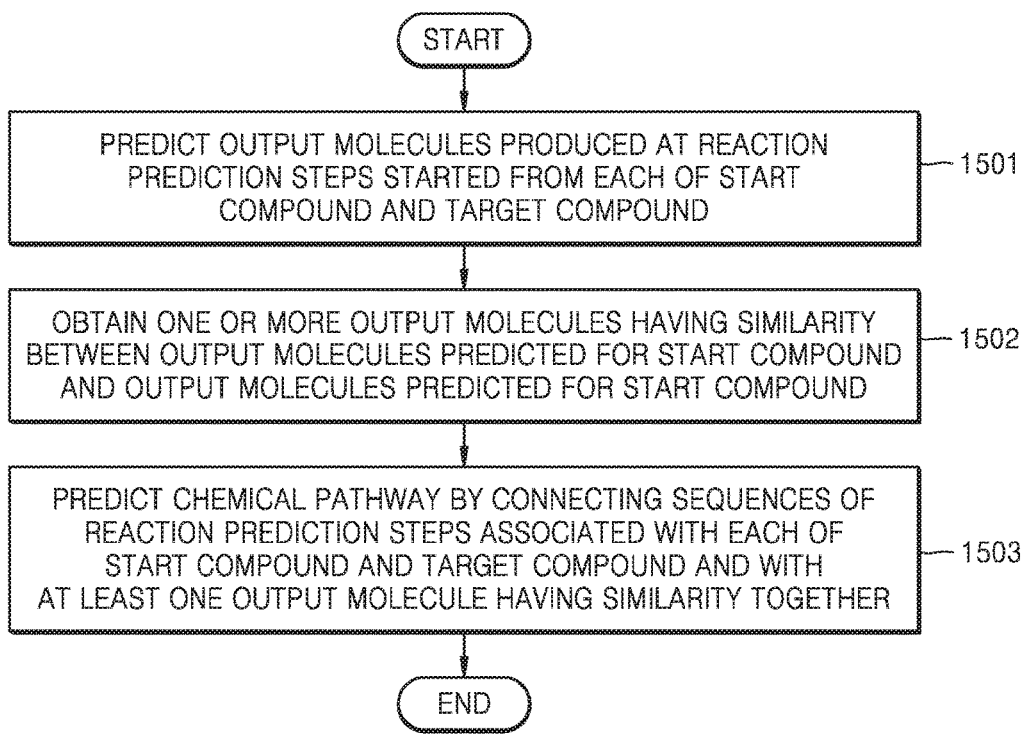
FIG. 15 is a schematic flowchart illustrating a method of prediction for a chemical pathway, according to another embodiment.

FIG. 15 is a schematic flowchart illustrating a method of prediction for a chemical pathway, according to another embodiment. The method of FIG. 15 may be a method performed in a time-series manner in the chemical pathway prediction device 1400 of FIG. 14.

In operation 1501, the processor 1401 predicts output molecules produced at reaction prediction steps started from each of the start compound and the target compound.

In operation 1502, the processor 1401 obtains one or more output molecules having similarity between the output molecules predicted from the start compound and the output molecules predicted from target compound.

In operation 1503, the processor 1401 predicts the chemical pathway by associating the order of the reaction prediction steps proceeded with the one or more output molecules that have similarity between the output molecules predicted from the start compound and the output molecules predicted from the target compound.

The embodiments of the present inventive concept may include a processor, a memory for storing and executing program data, a permanent storage such as a disk drive, a communication port for communication with an external device, and a user interface device including a touch panel, a key, and a button. Methods implemented by software modules or algorithms may be stored in a non-transitory computer-readable recording medium in the form of a computer-readable code or a program order that is executable by the processor. Here, the non-transitory computer-readable recording medium may include a magnetic storage medium (e.g., ROM, RAM, a floppy disk, a hard disk, and the like) or an optical readable medium (e.g., a CD-ROM, a digital versatile disc (DVD), and the like). The non-transitory computer-readable recording medium is distributed to computer systems connected to a network, and accordingly, computer-readable codes may be stored and executed according to a distribution method. A medium can be readable by a computer, stored by a memory, and include programs executed by a processor.

The present embodiments can be represented by functional block configurations and various processing operations. Such functional blocks can be implemented by the various numbers of hardware and/or software that executes particular functions. For example, the direct circuit configuration, such as a memory, a processing, a logic, or a look-up table that can execute various functions by controlling at least one microprocessor or using a different controlling device, can be described in the embodiments. Similarly to the components that can be executed in software programming or as software elements, various algorithms that are implemented by data structures, processes, routines, or a combination of other programming components are described in the present embodiments, and accordingly, such algorithms can be implemented by programming or scripting languages, such as C, C++, Java, or assembler. Functional aspects of the present inventive concept can be implemented with an algorithm that is executable on at least one processor. In addition, techniques in the related art for electronic settings, signal processing, and/or data processing can be described in the present embodiments. The terms "mechanism," "element," "means," and "configuration" can be widely used, and are not limited to mechanical and physical configurations. These terms can be linked to processors or the like, thereby including the meaning of a series software routines.

The specific executes described in the present embodiments are for exemplification purposes only, and are not intended to limit technical scope of any method. For the sake of brevity, conventional electronics, control systems, software development and other functional aspects of the systems may not be described in detail. Furthermore, the connecting lines, or connectors shown in the various figures presented are intended to represent exemplary functional relationships and/or physical or logical couplings between the various elements. It should be noted that many alternative or additional functional relationships, physical connections or logical connections may be present in a practical device.

The use of the terms "a" and "an" and "the" and similar referents in the context of describing the inventive concept (especially in the context of the following claims) are to be construed to cover both the singular and the plural. Furthermore, recitation of ranges of values herein are merely intended to serve as a shorthand method of referring individually to each separate value falling within the range, unless otherwise indicated herein, and each separate value is incorporated into the specification as if it were individually recited herein. Also, the operations of all methods described herein can be performed in any suitable order unless otherwise indicated herein or otherwise clearly contradicted by context. The inventive concept is not limited to the described order of the operations.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope as defined by the following claims.

What is claimed is:

1. A method for in silico prediction of one or more chemical pathways for transforming one or more start compounds to one or more target compounds, comprising the steps, implemented in at least one processor, of:
   multi-directionally predicting one or more output molecules, through one or more reaction prediction steps, produced by each of one or more inputs using a knowledgebase, wherein
      the one or more inputs comprise at least one of: the one or more start compounds, the one or more target compounds, and the predicted one or more output molecules,
      the one or more output molecules predicted to be produced at a previous reaction prediction step become input for a next reaction prediction step,
      the one or more output molecules are predicted at each of the reaction prediction steps by applying a set of one or more transformation rules, included in the knowledgebase, on the one or more inputs; and
      the one or more transformation rules comprise molecular transformations including transformation of a chemical moiety residing on a molecule, modification of at least one of chemical bonds, bond rearrangements, and chemical states, which undergo a reaction process;
   collecting all the multi-directionally predicted one or more output molecules into a set of one or more intermediate molecules, after each reaction prediction step;
   computing similarity between the multi-directionally predicted one or more output molecules within the set of one or more intermediate molecules to classify one or more groups of similar one or more output molecules; and
   identifying a representative member for each of the one or more groups of similar one or more output molecules in each reaction prediction step
   replacing each of the one or more groups of similar one or more output molecules within the set of one or more intermediate molecules with the identified representative member, thereby using the identified representative member and non-similar multi-directionally predicted one or more output molecules as one or more inputs for a next reaction prediction step; and
   connecting together the one or more start compounds, the one or more target compounds, the multi-directionally predicted one or more output molecules, and one or more sequences of the one or more reaction prediction steps, to predict the one or more chemical pathways, thereby reducing redundancy in pathway prediction computation and computed pathway data,
   wherein the one or more predicted chemical pathways comprise a sequential arrangement of the one or more reaction prediction steps governed by the set of one or more transformation rules applied on the one or more inputs for multi-directionally predicting the one or more output molecules at the each of the reaction prediction steps.

2. The method of claim 1, wherein a number of the one or more reaction prediction steps for transforming the one or more start compounds to the one or more target compounds is a preset number.

3. The method of claim 2, wherein the one or more reaction prediction steps are repeatedly performed on the one or more inputs until a total number of the one or more reaction prediction steps equals the preset number of the one or more reaction prediction steps for transforming the one or more start compounds to the one or more target compounds.

4. The method of claim 1, wherein the knowledgebase comprises: a list of reactions, one or more chemical moieties present in each reaction of the list of reactions, one or more changes taking place in the one or more chemical moieties present in the each reaction of the list of reactions during the reaction, a set of one or more transformation rules governing each of the listed reactions, and a set of one or more transformation rules represented by a unique list of one or more transformations.

5. The method of claim 1, further comprising sorting the predicted one or more chemical pathways based on at least one of: reaction feasibility, kinetics, and abundance of intermediates formed in the chemical pathway.

6. The method of claim 5, further comprising selecting one or more chemical pathways out of the sorted one or more chemical pathways based on at least one of: reaction feasibility, kinetics, and abundance of intermediates formed in the chemical pathway.

7. The method of claim 1, wherein the computing step is performed:
 after each of the reaction prediction steps; or
 after a preset number of the reaction prediction steps.

8. A device for in silico prediction of one or more chemical pathways for transforming one or more start compounds to one or more target compounds, comprising:
 one or more processors operatively coupled to a memory containing instructions which when executed by the one or more processors cause the one or more processors to perform steps comprising:
  multi-directionally predicting one or more output molecules, through one or more reaction prediction steps, produced by each of one or more inputs using a knowledgebase, wherein
   the one or more inputs comprise at least one of: the one or more start compounds, the one or more target compounds, and the predicted one or more output molecules,
   the one or more output molecules predicted to be at a previous reaction prediction step become input for a next reaction prediction step,
   the one or more output molecules are predicted at each of the reaction prediction steps by applying a set of one or more transformation rules, included in the knowledgebase, on the one or more inputs; and
   the one or more transformation rules comprise molecular transformations including transformations of a chemical moiety residing on a molecule, modification of at least one of chemical bonds, bond rearrangements, and chemical states, which undergo a reaction process;
  collecting all the predicted one or more output molecules into a set of one or more intermediate molecules, after each reaction prediction step;
  computing similarity between the multi-directionally predicted one or more output molecules within the set of one or more intermediate molecules to classify one or more groups of similar one or more output molecules; and
  identifying a representative member for each of the one or more groups of similar one or more output molecules;
  replacing each of the one or more groups of similar one or more output molecules within the set of one or more intermediate molecules with the identified representative member, thereby using the identified representative member and non-similar multi-directionally predicted one or more output molecules as one or more inputs for a next reaction prediction step; and
  connecting together the one or more start compounds, the one or more target compounds, the multi-directionally predicted one or more output molecules, and one or more sequences of the one or more reaction prediction steps, to predict the one or more chemical pathways, thereby reducing redundancy in pathway prediction computation and computed pathway data,
  wherein the one or more predicted chemical pathways comprise a sequential arrangement of the one or more reaction prediction steps governed by the set of one or more transformation rules applied on the one or more inputs for multi-directionally predicting the one or more output molecules at the each of the reaction prediction steps.

9. The device of claim 8, wherein the computing step is performed:
 after each of the reaction prediction steps; or
 after a preset number of the reaction prediction steps.

10. A method for in silico prediction of one or more chemical pathways for transforming one or more start compounds to one or more target compounds, comprising the steps, implemented in at least one processor, of:
 multi-directionally predicting one or more output molecules, through one or more reaction prediction steps, produced by each of one or more inputs using a knowledgebase, wherein
  the one or more inputs comprise at least one of: the one or more start compounds, the one or more target compounds, and the predicted one or more output molecules,
  the one or more output molecules predicted to be produced at a previous reaction prediction step become input for a next reaction prediction step,
  the one or more output molecules are predicted at each of the reaction prediction steps by applying a set of one or more transformation rules, included in the knowledgebase, on the one or more inputs, and
  the one or more transformation rules comprise molecular transformations including transformation of a chemical moiety residing on a molecule, modification of at least one of chemical bonds, bond rearrangements, and chemical states, which undergo a reaction process;
 after each reaction prediction step or after a preset number of reaction steps, computing similarity between the multi-directionally predicted one or more output molecules to classify one or more groups of similar one or more output molecules; and
 identifying a single representative member for each of the one or more groups of similar one or more output molecules in each reaction step;
 replacing each of the one or more groups of similar one or more output molecules with the identified single representative member, thereby using the identified single representative member and non-similar multi-directionally predicted one or more output molecules as one or more inputs for a next reaction prediction step; and
 connecting together the one or more start compounds, the one or more target compounds, the multi-directionally predicted one or more output molecules, and one or more sequences of the one or more reaction prediction steps, to predict the one or more chemical pathways, thereby reducing redundancy in pathway prediction computation and computed pathway data,
 wherein the one or more predicted chemical pathways comprise a sequential arrangement of the one or more reaction prediction steps governed by the set of one or more transformation rules applied on the one or more inputs for multi-directionally predicting the one or more output molecules at the each of the reaction prediction steps.

* * * * *